(12) United States Patent
Leeflang et al.

(10) Patent No.: US 12,649,028 B2
(45) Date of Patent: *Jun. 9, 2026

(54) INJECTION DEVICES AND SYSTEMS AND METHODS FOR USING THEM

(71) Applicant: CLPH, LLC, Palo Alto, CA (US)

(72) Inventors: Stephen A. Leeflang, Sandy, UT (US); Christian S. Eversull, Palo Alto, CA (US)

(73) Assignee: CLPH, LLC., West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/739,243

(22) Filed: Jun. 10, 2024

(65) Prior Publication Data

US 2025/0041516 A1     Feb. 6, 2025

Related U.S. Application Data

(63) Continuation of application No. 17/673,675, filed on Feb. 16, 2022, now Pat. No. 12,005,231, which is a (Continued)

(51) Int. Cl.
| | |
|---|---|
| *A61M 5/168* | (2006.01) |
| *A61M 5/145* | (2006.01) |
| *A61M 5/158* | (2006.01) |

(52) U.S. Cl.
CPC ...... *A61M 5/16813* (2013.01); *A61M 5/1452* (2013.01); *A61M 5/158* (2013.01); *A61M 5/168* (2013.01)

(58) Field of Classification Search
CPC .......... A61M 5/19; A61M 5/168; A61M 5/14; A61M 5/16813; A61M 5/1407; A61M 5/1452; A61M 5/158; A61M 5/16804; A61M 5/2066; A61M 5/284; A61M 5/16827; A61M 5/31596; A61M 5/14236; A61M 5/142; A61M 5/14212; A61M 5/14216; A61M 5/1424; A61M 5/145; A61M 5/16877; A61M 5/315; A61M 5/488; A61M 2025/0057; A61M 2025/0073; A61M 2025/0091; A61M 2025/0089; A61M 25/0084; A61M 25/0071;

(Continued)

(56) References Cited

U.S. PATENT DOCUMENTS

| | | | |
|---|---|---|---|
| 11,253,646 B2 * | 2/2022 | Leeflang ............... | A61M 5/168 |
| 2002/0049448 A1 * | 4/2002 | Sand .................. | A61B 17/8819 606/92 |
| 2004/0147873 A1 * | 7/2004 | Gellman ........... | A61M 5/31596 604/82 |

* cited by examiner

*Primary Examiner* — Kevin C Sirmons
*Assistant Examiner* — Alexandra Lalonde
(74) *Attorney, Agent, or Firm* — William A. English; Vista IP Law Group LLP

(57) ABSTRACT

Systems and methods are provided for injecting one or more agents into tissue within a patient's body. In one embodiment, an injection device is provided that includes an outer tubular member comprising a proximal end, a distal end sized for introduction into the patient's body, and a lumen extending between the proximal end and the distal end; a relatively small cross-section needle tip extending distally beyond the distal end; and an internal pressure release member slidably disposed within the lumen between a distal position and a proximal position to prevent viscous injectate from expressing from the needle tip.

10 Claims, 2 Drawing Sheets

Related U.S. Application Data continuation of application No. 16/145,080, filed on Sep. 27, 2018, now Pat. No. 11,253,646.

(60) Provisional application No. 62/563,826, filed on Sep. 27, 2017.

(58) Field of Classification Search
CPC .......... A61M 2005/14506; A61M 2005/1585; A61M 2005/3103; A61M 2005/3107; A61M 2005/3132; A61B 17/8802; A61B 17/8805; A61B 17/8822; A61B 17/8819; A61B 17/00491; A61B 17/8825; A61B 17/320775; Y10T 137/87652
See application file for complete search history.

INJECTION DEVICES AND SYSTEMS AND METHODS FOR USING THEM

RELATED APPLICATION DATA

This application is a continuation of co-pending application Ser. No. 17/673,675, filed Feb. 16, 2022, and issuing as U.S. Pat. No. 12,005,231, which is a continuation of application Ser. No. 16/145,080, filed Sep. 27, 2018, now U.S. Pat. No. 11,253,646, which claims benefit of provisional application Ser. No. 62/563,826, filed Sep. 27, 2017, the entire disclosures of which are expressly incorporated by reference herein.

FIELD OF THE INVENTION

The present invention relates generally to apparatus, systems, and methods for performing medical procedures, and more particularly to needles or other injection devices, and to systems and methods for injecting one or more agents into tissue, e.g., viscous injectates, into tissue, e.g., within a patient's heart or other location, using such injection devices.

BACKGROUND

While injection devices and needle systems have been in use for many years, recent developments in minimally invasive procedures require needle systems capable of accessing distant or difficult to access regions of the body, capable of delivering agents of high viscosity (e.g., chemo-embolization agents, depot drug formulations, fillers, etc.), capable of delivering agents with low shear (cells), and/or capable of delivering agents at high flow rates.

Injection devices may include a simple needle attached to a syringe, a needle assembly designed to pass through the working channel of an endoscope or catheter or other minimally invasive introduction device, and/or a needle incorporated into a more complicated device. In such cases, injecting viscous fluids into a body cavity, space, or tissue involves a number of unique challenges compared to injecting non-viscous fluids. These challenges/problems include, among others, efficient movement of the fluid with minimized pressure requirement and/or shear force, clog prevention, clog elimination/clearing, multiple sequential injections, injection of one or more additional, in some cases less viscous, fluids sequentially or intermittently without significant cross contamination, etc.

Further, the need for flexible catheter-based needle injection systems has increased in recent years given the proliferation of potential injectable materials (e.g., stem cells, ablative agents, chemotherapeutic agents, bio-polymers, other pharmaceuticals, etc.). The benefits of these materials frequently depend on the ability to precisely target their delivery to specific anatomical locations, which depends on many common catheter challenges most especially flexibility. Additionally, in the case of viscous fluids or high volume injections, the need arises for a design to balance two conflicting objectives—a small needle to minimize trauma, etc. and a large diameter to enable ease of injection, e.g., to maximize or permit adequate flow at a reasonable pressure, e.g., which can be easily generated by a handheld syringe.

In addition, due to the viscous nature of some injectates, the high pressure required to inject may not immediately be released from the needle or injection system upon removal of injection pressures. Additionally, the "static friction" of viscous injectates in the needle and needle body may be such that a full vacuum (e.g., −14.7 psi) does not move the injectate and, hence, the application of vacuum may not be sufficient to release the built-up high pressure inside the needle or over the full length of the injection device. Finally, because there is a capacitance/expansion/compression to the system (both in the injectate, which may have air or other gas bubbles suspended or dissolved therein, and/or otherwise compressible, and the needle, needle body, and/or injection path), the built-up high pressure may cause a slow but unacceptable expression of injectate over an extended period of time, e.g., two to eight (2-8) minutes, e.g., between multiple injections, which may result in the injectate being exposed within the patient's vasculature or other undesired location within the patient's body.

Therefore, apparatus and methods that facilitate injection of viscous materials would be useful.

SUMMARY

The present invention is directed to apparatus, systems, and methods for performing minimally invasive medical procedures. More particularly, the present invention is directed to needles or other injection devices, and to systems and methods for injecting one or more agents into tissue, e.g., viscous injectates into tissue, e.g., within a patient's heart or other location, using such injection devices.

In accordance with one embodiment, a device is provided for injecting a viscous injectate into tissue within a patient's body that includes a tubular outer member comprising a proximal end, a distal end sized for introduction into a patient's body, and a lumen extending between the proximal and distal ends; a needle or other tubular extension extending distally beyond the distal end to a distal tip, the tubular extension having a cross-section smaller than the distal end and a passage communicating between the lumen and an outlet in the distal tip; and an inner pressure release member slidably disposed within the lumen between a distal position and a proximal position to prevent the injectate from expressing from the distal tip after delivery at a target location.

Optionally, the device may also include a manifold coupled to the proximal end including a source of injectable material and an actuator for selectively directing the injectable material from the source through the lumen and out the outlet. In one embodiment, a proximal end of the pressure release member may extend from the proximal end of the outer member such that the pressure release member may be manually retracted from the distal position, during delivery of the injectate, to the proximal position, after delivery of the injectate, e.g., to release pressure and/or remove residual injectate from the passage.

In accordance with another embodiment, a system is provided for injecting a viscous injectate into tissue within a patient's body that includes an outer member comprising a proximal end, a distal end sized for introduction into a patient's body, and a lumen extending between the proximal and distal ends; a needle tip extending distally beyond the distal end to a distal tip and including a passage communicating between the lumen and an outlet in the distal tip; a source of viscous injectate coupled to the proximal end and communicating with the lumen for delivering the injectate through the lumen and passage and out the outlet; and an inner member slidably disposed within the lumen, the inner member comprising a proximal end disposed adjacent the outer member proximal end and a distal end disposed within the lumen, the inner member having an outer profile smaller than inner profile of the lumen such that the injectate passes through the lumen around the inner member, the inner member movable from a distal position wherein the inner member distal end is disposed adjacent the passage during delivery of the injectate and a proximal position in which the inner member distal end is directed proximally away from the passage after delivery of the injectate to prevent the injectate from expressing from the distal tip.

In accordance with yet another embodiment, a method is provided for injecting one or more agents into tissue, e.g., into tissue within a patient's heart and/or other location, using an injection device including an outer member including a proximal end, a distal end, and a lumen extending therebetween a, needle tip extending from the distal end, and a pressure release member slidably disposed within the lumen. The distal end of the outer member may be introduced into a body lumen adjacent a target injection site, the needle tip may be inserted into tissue at the target injection site, and, with a distal end of the pressure release member disposed adjacent the needle tip, injectate may be delivered from a source through the lumen around the pressure release member and through the needle tip into the tissue. After delivering the injectate, the pressure release member may be withdrawn proximally such that the pressure release member distal end moves proximally away from the passage to prevent injectate from expressing out the needle tip.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which.

DETAILED DESCRIPTION OF THE EXEMPLARY EMBODIMENTS

Figures 1, 2, 3:
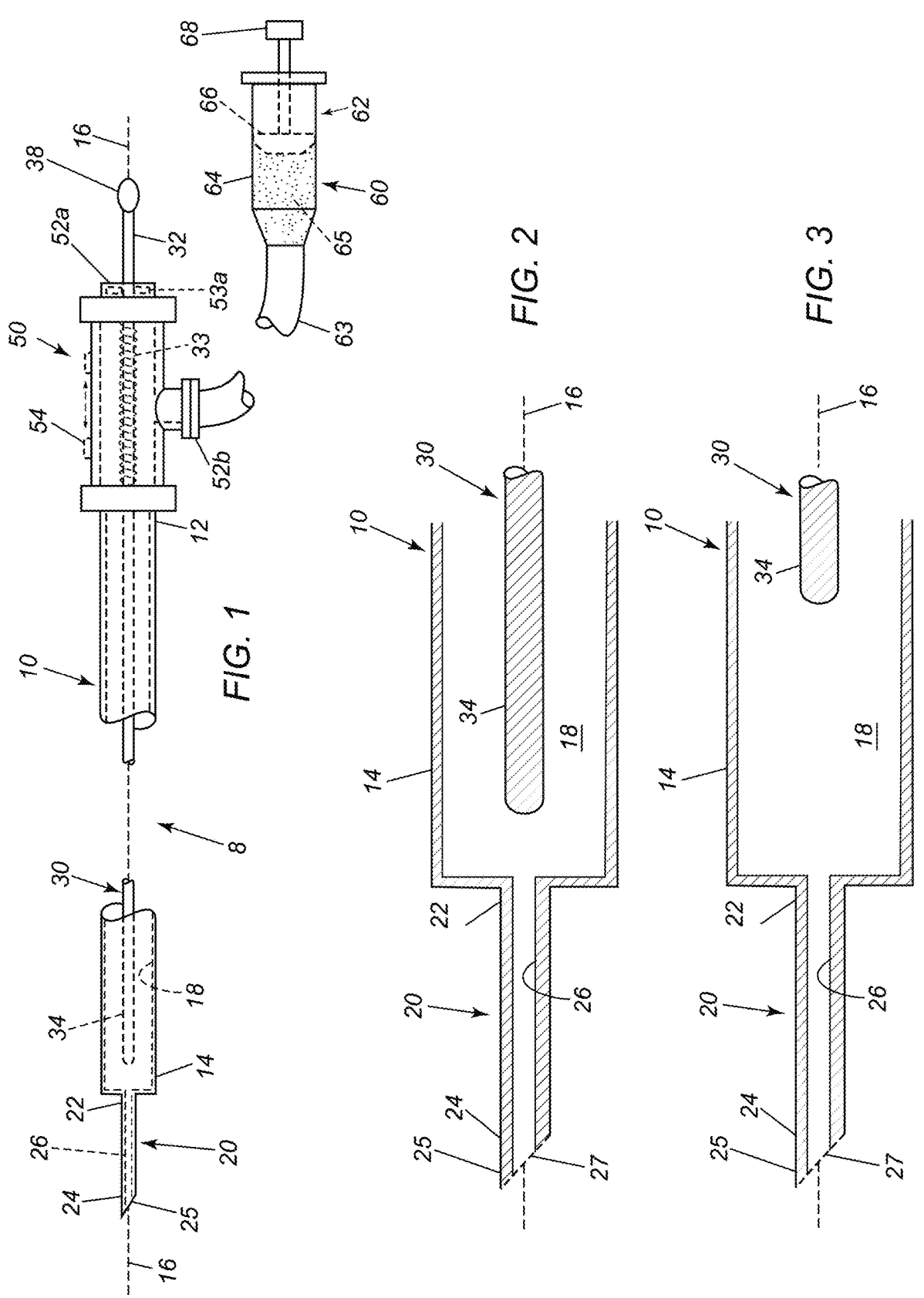
FIG. 1 is a side view of an exemplary embodiment of an injection device including an outer tubular member terminating in a low profile needle tip and an internal pressure release member slidably disposed within the tubular member.
FIG. 2 is a cross-sectional detail of the injection device of FIG. 1 showing the pressure release member in an initial distal position adjacent the needle tip.
FIG. 3 is a cross-section detail of the injection device of FIG. 1 showing the pressure release member in a proximal position to prevent expression of viscous injectate from the needle tip.

Turning to the drawings, FIG. 1 shows an exemplary embodiment of a needle or injection device 8 for performing a medical procedure within a patient's body, e.g., for injecting one or more agents into tissue, e.g., into the wall of a patient's heart (not shown). For example, the device 8 may be used to deliver viscous fluids, gels, agents, and/or other flowable materials, e.g., including one or more diagnostic and/or therapeutic compounds (generally referred to herein as "injectates").

As shown, the injection device 8 generally includes an outer shaft or tubular member 10 including a proximal end or portion 12, a distal end or portion 14 sized for introduction into a patient's body, one or more lumens, e.g., lumen 18, extending between the proximal and distal ends 12, 14, a relatively low profile distal extension or needle tip 20, and an inner release member 30. In addition, the device 8 may include a manifold or handle 50 coupled to the proximal end 12, e.g., including one or more ports 52 and/or actuators (not shown), and a source of injectate 60. Optionally, one or more additional components or devices may be provided, e.g., an access or delivery sheath, endoscope, one or more stylets, and/or one or more guidewires or rails (not shown) to provide a system for performing a procedure, as described elsewhere herein.

Generally, the outer shaft 10 is an elongate tubular member defining a central longitudinal axis 16 extending between the proximal and distal ends 12, 14, and one or more lumens 18 extending between the proximal and distal ends 12, 14. In the embodiment shown in FIG. 1, the outer shaft 10 may include a single lumen 18 formed by the wall of the shaft 10. Alternatively, the shaft 10 may include one or more additional lumens within the wall of the shaft 10 (not shown), if desired, or the shaft 10 may be formed as one or more separate tubular members, e.g., bladders or sleeves (also not shown), within an outer coil or tubular shaft, e.g., similar to those described in U.S. Publication No. 2017/0119956, the entire disclosure of which is expressly incorporated by reference herein. For example, in one alternative, the outer shaft 18 may include a secondary lumen (not shown) that may be used to deliver contrast or other fluids out the needle tip 20.

The outer shaft 10 may be substantially flexible, semi-rigid, and/or rigid along its length, and may be formed from a variety of materials, including plastic, metal, and/or composite materials, as is well known to those skilled in the art. In addition, the shaft 10 may have a substantially uniform outer diameter (or other cross-section) between the proximal and distal ends 12, 14, or the diameter may vary along the length of the shaft 10.

For example, in one embodiment, the shaft 10 may have a substantially uniform construction and size along its length between the proximal and distal ends 12, 14. Alternatively, a distal portion of the shaft 10, e.g., having a length of about ninety centimeters (90 cm) or more, immediately adjacent to or spaced a predetermined distance from the needle tip 20, may be substantially flexible to facilitate advancement through tortuous anatomy, while a proximal region, e.g., extending a predetermined distance from the proximal end 12, e.g. about thirty centimeters (30 cm) or more, may be semi-rigid or rigid to enhance pushability and/or torqueability of the outer shaft 10 without substantial risk of buckling or kinking. Optionally, the lumen 18 may include lubricious material or may be formed from one or more layers of thermoplastic or other polymeric material including one or more coatings on the inner surface thereof having desired properties, e.g., a hydrophilic and/or lubricious coating, e.g., similar to the liners disclosed in U.S. Pat. Nos. 7,550,053 and 7,553,387, and U.S. Publication No. 2009/0126862, the disclosures of which are expressly incorporated by reference herein.

Figure 4:
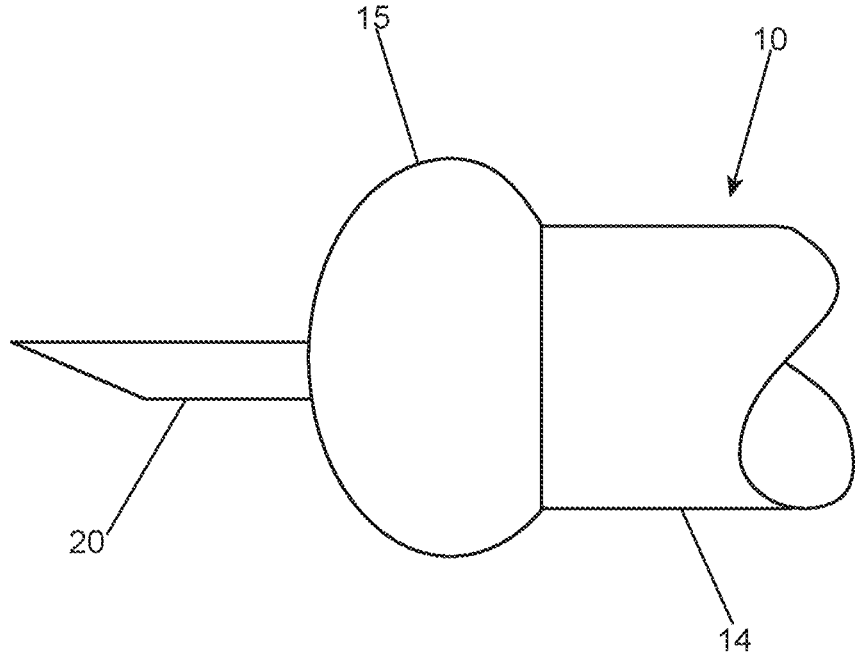
FIG. 4 shows an example of a distal stop on the distal end of the outer shaft of the injection device shown in FIG. 1.

Optionally, as shown in FIG. 4, a distal stop 15 may be provided on the distal end 14 of the outer shaft 10, and the needle tip 20 may extend from the distal stop 15. In an exemplary embodiment, the distal stop 15 may be a bulbous, rounded, and/or other atraumatically shaped element coupled to the distal end 14 of the outer shaft 10. The tissue stop 15 may have a diameter or other cross-section that is larger than the distal end 14 and/or may include a rounded or substantially flat distal surface that is substantially larger in surface area than the cross-section of the needle tip 20, e.g., to provide tactile feedback when the needle tip 20 is inserted into tissue and/or limit insertion of the needle tip 20 into tissue.

In addition or alternatively, the shaft 10 may include one or more features to enhance visibility under ultrasound, MRI or other imaging modalities, e.g., by providing one or more radiopaque markers on and/or doping one or more regions adjacent the needle tip 20, e.g. as known in the art. For example, one or more radiopaque markers (not shown) may be provided, e.g., at the base of the needle tip 20, on the distal end 14, and/or on the distal stop, to facilitate identification of the needle tip 20 and/or depth of penetration into tissue.

The needle tip 20 may be coupled to and/or otherwise extend distally from the distal end 14 of the shaft 12 (or the distal stop), e.g., such that the shaft 12 defines a main portion of the device 10 and the needle tip 20 defines a smaller penetrating portion. In one embodiment, the needle tip 20 may be a single tubular body having a first end 22 coupled to the distal end 14 of the shaft 12, and a second end 24 terminating in a distal tip 25 having a beveled, multi-faceted grind, trocar grind, or other sharpened shape, as desired to facilitate penetration into tissue. A passage or lumen 26 may extend from the first end 22 to one or more outlets, e.g., outlet 27, in the distal tip 25. In addition or alternatively, one or more outlets may be provided along the outer surface of the needle tip 20, e.g., adjacent to or instead of the outlet 27. In addition or alternatively, the needle tip 20 may be substantially straight, e.g., as shown in FIG. 1, or may be formed in a fixed curved or other curvilinear shape, e.g., to facilitate securement and/or accessing tissue not directly aligned with the longitudinal axis 16.

In an exemplary embodiment, the needle tip 20 may be formed from a section of hypotube or other uniform tubular body, similar to conventional needles e.g., formed from metal, such as stainless steel, plastic, or composite material, having desired mechanical properties, e.g., sufficient column strength to allow the needle tip 20 to be directed into tissue by manipulating the shaft 10 from the proximal end 12. In exemplary embodiments, the needle tip 20 may have a relatively thin wall, e.g., no larger than 25 gauge, or no larger than 32 gauge, to reduce the rigidity of the needle tip 20, if desired. The proximal end 22 of the needle tip 20 may be attached to the distal end 14 of the shaft 10, e.g., by one or more of interference fit, cooperating connectors, bonding with adhesive, fusing, welding, soldering, and the like, e.g., such that the needle tip 20 is centered on the distal end 14 and extends substantially parallel to the longitudinal axis 16. Alternatively, the distal extension 20 may be coupled to a separate manifold or other connector (not shown), e.g., an enlarged distal stop (not shown), which may include one or more internal chambers or passages communicating between the lumen 18 and the passage 26, e.g., similar to the devices described in U.S. Publication No. 2017/0119956.

Optionally, a tapered or flared transition (not shown) may be provided at the first end 22 of the needle tip 20 to facilitate connection to the distal end 14 of the shaft 10. Alternatively, a blunt transition may be provided if desired, e.g., to provide a stop, which may provide tactile feedback or otherwise prevent directing the needle tip 20 too deep into tissue.

Thus, in an exemplary embodiment, the entire outer shaft 10 or at least the distal end 14 of the outer shaft 10 may have a first outer diameter and the needle tip 20 may have a second outer diameter that is smaller than the first outer diameter. In exemplary embodiments, the first outer diameter may be between about 0.040-0.080 inch (1.0-2.0 mm)

and the second outer diameter may be between about 0.010-0.025 inch (0.025-0.0625 mm), e.g., about ten to fifty percent (10-50%) smaller than the first outer diameter. Similarly, the outer shaft 10 may have a first length between the first and second ends 12, 14 that is substantially longer than a second length of the needle tip 20, e.g., such that the shaft 10 may extend from an access site, e.g., a percutaneous access site in the patient's skin through the patient's vasculature to a target treatment site, e.g., a chamber within the patient's heart. In exemplary embodiments, the first length may be between about forty and one hundred forty centimeters (40-140 cm) and the second length may be between about two and fifteen millimeters (2-15 mm), e.g., not more than about five millimeters (5 mm).

One potential advantage of having the outer shaft 10 larger than the distal extension 20 is that the lumen 18 of the device 8 may have a relatively larger diameter along most of the length of the device 8, e.g., along the entire length of the outer shaft 10 if the outer shaft 10 has a substantially uniform diameter between the proximal and distal ends 12, 14. For example, if a single lumen 18 is provided in the outer shaft 10, the inner diameter of the lumen 18 may be maximized, which may reduce friction for materials passing through the lumen 18, which may be particularly useful for viscous fluids or to reduce shear on fluids passing through the lumen 18. The passage 26 through the needle tip 20 may have a diameter substantially smaller than the lumen 18 but, given its relatively short length, may add minimal resistance to deliver such fluids. Thus, with the resistance to flow lower within the lumen 18 of the outer shaft 10 than within the passage 26 of the needle tip 20, the overall force needed to deliver the fluids may be reduced, as compared to a uniform diameter lumen sized similar to the passage 26.

With additional reference to FIGS. 2 and 3, the inner release member 30 generally is an elongate solid or hollow wire or other elongate member slidably disposed within the lumen and including a proximal end 32 and a distal end 34. The inner member 30 may have a substantially uniform diameter along its length or may, alternatively, comprise a variable diameter, e.g. a relatively smaller proximal diameter (e.g., to reduce resistance to fluid flow) and a relatively larger distal diameter (e.g., to achieve greater volume displacement and release of pressure with less axial translation).

In addition or alternatively, the inner member 30 may include a relatively uniform stiffness along its length. Alternatively, the inner member 30 may include variable stiffness along its length, e.g., a relatively stiffer proximal segment (e.g., to achieve greater pushability) and a relatively more flexible distal segment (e.g., to avoid damaging the lumen 18 or outer shaft 10 when passing through and/or to impart greater flexibility to the distal end 14).

The inner member 30 may pass through the lumen 18 relatively concentrically. Alternatively, the inner member 30 may be positioned away from the central axis of the lumen 18, e.g., in the event that there are one or more other elements passing through the lumen 18, such as an accessory infusion lumen.

Optionally, the inner member 30 may include and inflatable element (not shown), which may be subsequently be deflated after injection, e.g., to cause volume displacement distally with the lumen 18. For example, the inner member 30 may include a relatively small diameter tubular proximal element have an inner lumen for passage of inflation fluid and a distally positioned inflatable element (not shown), e.g., a balloon on the distal end 34. The inner member 30 may contain a fluid, e.g., air, nitrogen, saline, and the like, that is relatively less viscous than the injectate passing through the lumen 18. During injection of the injectate, the inflatable element (not shown) may be inflated and subsequently deflated, e.g., passively or under vacuum, to cause a volume displacement and pressure release distally within the lumen 18.

The inner member 30 may have sufficient length that the proximal end 32 extends from or is disposed within the handle 50 and the distal end 34 is disposed adjacent the passage 26. The inner member 30 may have an outer diameter or other cross-section that is smaller than the inner diameter of the lumen 18 such that injectate may be delivered through the lumen around the inner member 30. In an exemplary embodiment, the inner member 30 may have an outer diameter of not more than 0.014 inch (0.35 mm) and the lumen 18 may have an inner diameter of at least about 0.022 inch (0.55 mm) to provide sufficient clearance that viscous materials may be delivered through the lumen 18 around the inner member 30.

The inner member 30 may be slidably disposed within the outer shaft 10 between a distal position where the distal end 34 is disposed immediately proximal to the passage 26 of the needle tip 20, e.g., as shown in FIG. 2, and a proximal positon, wherein the distal end 34 is displaced a minimum distance from the passage 26, e.g., as shown in FIG. 3.

In the embodiment shown in FIG. 1, the handle 50 includes a port 52a communicating with the lumen 18 through which the proximal end 32 of the inner member 30 is slidably disposed. In an exemplary embodiment, the port 52a may include one or more seals, e.g., hemostatic seal 53a, to provide a fluid-tight seal around the inner member 30 and prevent fluid within the lumen 18 from escaping out the port 52a. In this embodiment, a hub or handle 38 may be provided on the proximal end 32 of the inner member 30 to facilitate manipulation of the inner member between the distal and proximal positions.

Optionally, one or more stops (not shown) may be provided within the handle 50 and/or on the proximal end 32 to limit movement of the inner member 30 between the distal and proximal positions. Alternatively, the inner member 30 may be removable entirely from and insertable into the outer member 20 via the port 52a. In a further alternative, the proximal end 32 of the inner member 30 may be disposed within the handle 50 and coupled to an actuator 54 (shown in phantom in FIG. 1), e.g., a slider, dial, and the like, that may be manipulated to move the inner member 30 between the distal and proximal positions. In another alternative, a biasing mechanism, e.g., a spring 33, ratchet, and/or other device (not shown) may be provided in the handle 50 that may selectively bias the inner member 30 to one or both of the distal and proximal positions during use, as described elsewhere herein.

As shown in FIG. 2, in the distal position, the distal end 34 of the inner member 30 may be spaced apart a predetermined distance from the entrance to the passage 26, e.g., between about one and fifty millimeters (1.0-50 mm), such that injectate passing through the lumen 18 may easily enter the passage 26 with minimal additional resistance. Alternatively, the distal end 34 of the inner member 30 may be smaller than the passage 26 such that the distal end 34 may be at least partially received within the passage 26 in the distal position (not shown). In the proximal position shown in FIG. 3, the distal end 34 may be retracted a predetermined distance, e.g., between about ten and five hundred millimeters (10-500 mm), sufficient to prevent undesired expression of the injectate from the needle tip 20 after an injection, as described elsewhere herein.

With continued reference to FIG. 1, the handle 50 may also include a side port 52b also communicating with the lumen 18, which may be coupled to the source of injectate 60. Optionally, the side port 52b may include one or more connectors, e.g., a Luer fitting and the like (not shown), such that the source of injectate 60 may be removably coupled to the side port 52b. Alternatively, a manifold (not shown) may be provided on the proximal end 12 of the outer shaft 10, e.g., integrated into the handle 50, to contain and/or deliver the injectate, e.g., as disclosed in U.S. Publication No. 2017/0119956.

In an exemplary embodiment, the source 60 may be a syringe 62 including a barrel 64 containing injectate 65, e.g., connected to the side port 52b by tubing 63, and a piston 66 on a distal end of a plunger 68 slidably disposed within the barrel 64 that may be depressed to deliver the injectate 65 through the tubing 66 and side port 52b into the lumen 18. Alternatively, other actuators may be provided, if desired. For example, for viscous materials, a screw actuator (not shown) may be provided to advance the piston 66, which may be provide a mechanical advantage than directly manipulating the piston 66 using the plunger 68, or a motorized pump or other driver (not shown) may be provided.

With further reference to FIG. 1, the device 8 may include a component (e.g., an auxiliary tube, passage, or lumen, not shown) configured to deliver a relatively low viscosity fluid to the distal end of the lumen 18, e.g., for the purpose of reducing or eliminating the inflow of material (e.g., blood) into the passage 26 as a result of volume displacement within the lumen 18. Flow of fluid through the component may be controlled, e.g., according to flow and/or pressure, e.g., in order achieve adequate pressure release within the lumen 18. Alternatively, or in addition, the device 8 may include a mechanism (not shown) for temporarily occluding the passage 26 or intermittently flushing the passage 26, e.g., to prevent inflow of blood into the passage 26 during the release of pressure within the lumen 18 and/or to eliminate blood from the passage 26 after relative pressure equilibrium has been achieved.

During use, the injection device 8 may be used to deliver injectate into a patient's body, e.g., into tissue within the wall of the heart, adjacent vessels of a patient's vasculature, and the like. For example, the distal end 14 may be introduced into a patient's body, e.g., into a chamber of the patient's heart (not shown), via one or more access sheaths, guidewires, and the like, and positioned as desired. Optionally, the distal end 14 and needle tip 20 may be positioned and/or otherwise oriented towards a target injection site using external imaging, e.g., fluoroscopy and the like, using one or more markers on the distal end 14 and/or needle tip 20. Optionally, contrast material may be delivered via the device 8 to facilitate such imaging and/or positioning, e.g., via the lumen 18 or, alternatively, via a secondary lumen.

Once positioned, the device 8 may be advanced to inserting the needle tip 20 into tissue at the target injection site. Under visualization, the needle tip 20 may be inserted a desired depth and/or a substantially flat distal surface of the distal end 14 (or distal stop) surrounding the needle tip 20 may contact a wall of the body lumen to limit penetration of the needle tip 20 into the tissue.

With the pressure release member 30 in the distal position, i.e., with the distal end 34 disposed adjacent the passage 26 as shown in FIG. 2, injectate may be delivered from the source 60 through the lumen 18 around the pressure release member 30 into the passage 26 and out the outlet 27 into the tissue. As described elsewhere herein, with viscous materials, substantial pressure may be required to deliver the injectate through the lumen 18 and passage 26 into the tissue.

After delivering the injectate, the pressure release member 30 may be withdrawn proximally such that the distal end 34 moves proximally away from the passage 26, as shown in FIG. 3, to prevent injectate from expressing out the needle tip 20. For example, the action of withdrawing the distal end 34 may create additional available space within the lumen 18 adjacent the passage 26 to absorb and/or relieve residual pressure, e.g. due to the compressibility of the injectate and/or system. In addition, surface tension between the distal end 34 and the surrounding residual injectate and/or the viscosity of the injectate may pull or otherwise remove some of the injectate proximally away from the passage 26, thereby minimizing the risk that injectate leaks or escapes from the outlet 27.

For example, in one method, the hub 38 on the proximal end 32 of the inner member 30 may be pulled manually relative to the handle 50 to withdraw the inner member to the proximal position. Alternatively, the inner member 30 may be coupled to an actuator 54, which may be used to withdraw the inner member 30. Once withdrawn, the needle tip 20 may be removed from the tissue and the device 8 may be withdrawn from the patient's body or alternatively, the distal end 14 may be directed to another location where another injection is desired. In this alternative, once the needle tip 20 is positioned and inserted into the next target injection site, the inner member 30 may be advanced back to the distal position before delivering the injectate (since any residual injectate that escapes during advancement of the inner member 30 will simply be delivered into the target tissue).

Alternatively, a biasing mechanism 33 may be coupled to the inner member 30 such that the inner member 30 is automatically withdrawn from the distal position to the proximal position after delivering the injectate. For example, pressure from delivery of the injectate may activate the biasing mechanism 33 such that, upon removal of the pressure after the injection, the biasing mechanism 33 may automatically direct the inner member 30 to the proximal position. If an additional injection is desired, the biasing mechanism 33 may be reset, e.g., after inserting the needle tip 20 into another target injection site, to advance the inner member 20 back to the distal position before delivery. In a further alternative, the biasing mechanism 33 may bias the inner member 30 to the proximal position and pressure or actuation during delivery of the injectate may advance the inner member 30 temporarily to the distal position until the injection is complete.

Although particularly useful for performing injections within a chamber of a heart, the needle devices and systems described herein may be used to perform other procedures, e.g., elsewhere within a patient's cardiovascular system or other locations within a patient's body, such as the lungs, liver, gastrointestinal tract, etc.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A device for injecting a viscous injectate into tissue within a patient's body, the device comprising:
   an outer member comprising a proximal end, a distal end sized for introduction into a patient's body, and a lumen extending between the proximal end and the distal end;
   a needle tip extending distally beyond the distal end to a distal tip and including a passage communicating between the lumen and an outlet in the distal tip;
   a handle on the proximal end including a port communicating with the lumen and connectable to a source of viscous injectate for delivering the injectate through the port, the lumen, and the passage and out the outlet; and
   an inner member slidably disposed within the lumen, the inner member comprising a proximal end disposed adjacent the outer member proximal end and a distal end disposed within the lumen, the inner member having an outer profile smaller than an inner profile of the lumen such that the injectate passes through the lumen around the inner member, the inner member movable from a distal position wherein the inner member distal end is disposed immediately proximal to the passage during delivery of the injectate around the inner member to a proximal position in which the inner member distal end is directed proximally away from the passage after delivery of the injectate to prevent the injectate from expressing from the distal tip.

2. The device of claim 1, wherein the needle tip has a cross-section smaller than a cross-section of the distal end of the outer member.

3. The device of claim 1, further comprising a distal stop on the outer member distal end, the needle tip extending distally beyond the distal stop.

4. The device of claim 3, wherein the distal stop comprises one or more passages communicating between the lumen and the passage of the needle tip.

5. The device of claim 3, wherein the distal stop comprises a body having an outer dimension larger than an outer dimension of the outer member distal end.

6. The device of claim 3, wherein the distal stop comprises a rounded or flat distal surface adjacent the needle tip to limit penetration of the needle tip into the tissue.

7. The device of claim 1, further comprising a release member port on the handle through which the inner member is slidably disposed such that the inner member proximal end is exposed from the handle and may be manipulated manually to move the inner member from the distal position to the proximal position.

8. The device of claim 7, further comprising one or more seals in the release member port to provide a fluid-tight seal and prevent fluid within the lumen from escaping out the release member port.

9. The device of claim 7, further comprising a hub on the inner member proximal end to facilitate manipulating the inner member.

10. The device of claim 1, further comprising an actuator on the handle coupled to the inner member for directing the inner member from the distal position to the proximal position.

* * * * *